(12) United States Patent
Liu et al.

(10) Patent No.: US 11,331,517 B2
(45) Date of Patent: May 17, 2022

(54) MULTI-LEAF COLLIMATOR AND RADIATION THERAPY DEVICE

(71) Applicant: SHANGHAI UNITED IMAGING HEALTHCARE CO., LTD., Shanghai (CN)

(72) Inventors: Jian Liu, Shanghai (CN); Kun Yang, Shanghai (CN); Jian Zhang, Shanghai (CN); Yanfang Liu, Shanghai (CN); Cheng Ni, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 155 days.

(21) Appl. No.: 16/801,140

(22) Filed: Feb. 25, 2020

(65) Prior Publication Data
US 2020/0360727 A1 Nov. 19, 2020

(30) Foreign Application Priority Data
May 15, 2019 (CN) .......................... 201910407804.6

(51) Int. Cl.
*A61N 5/10* (2006.01)
*G21K 1/04* (2006.01)

(52) U.S. Cl.
CPC ......... *A61N 5/1045* (2013.01); *A61N 5/1036* (2013.01); *A61N 5/1048* (2013.01); *A61N 5/1081* (2013.01); *G21K 1/046* (2013.01)

(58) Field of Classification Search
CPC ............ G21K 1/02; G21K 1/025; G21K 1/04; G21K 1/046; G21K 5/04; A61N 5/10; A61N 5/103; A61N 5/1036; A61N 5/1042; A61N 5/1045; A61N 5/1047; A61N 5/1048; A61N 5/1064; A61N 5/1065;
(Continued)

(56) References Cited

U.S. PATENT DOCUMENTS 4,739,173 A 4/1988 Blosser et al.
5,418,827 A 5/1995 Deasy et al.
(Continued)

FOREIGN PATENT DOCUMENTS

CA 2339534 C 2/2004
CN 2467120 Y 12/2001
(Continued)

OTHER PUBLICATIONS

First Office Action in Chinese Application No. 201910407804.6 dated Aug. 17, 2020, 11 pages.

*Primary Examiner* — Anastasia Midkiff
(74) *Attorney, Agent, or Firm* — Metis IP LLC

(57) ABSTRACT

The present disclosure generally relates to a multi-leaf collimator. The multi-leaf collimator may include a set of leaves installed in a cavity, each leaf of the set of leaves having a length along a first direction. At least a portion of the set of leaves may extend beyond the cavity along the first direction. The set of leaves may be arranged along a second direction, the second direction being different from the first direction. A length of a target leaf of the set of leaves may be less than a length of a reference leaf of the set of leaves. The target leaf may be located in an end portion of the set of leaves along the second direction. The length of the set of leaves may conform to the shape of a maximum therapeutic radiation field.

20 Claims, 9 Drawing Sheets

(58) Field of Classification Search
CPC ...... A61N 5/1067; A61N 5/1077; A61B 6/06; A61B 6/405
See application file for complete search history.

(56) References Cited

U.S. PATENT DOCUMENTS

| | | | |
|---|---|---|---|
| 5,438,454 | A | 8/1995 | Ludewigt et al. |
| 2004/0096038 | A1 | 5/2004 | Brown et al. |
| 2005/0063516 | A1 | 3/2005 | Kato et al. |
| 2007/0040127 | A1 | 2/2007 | Brahme et al. |
| 2008/0165928 | A1 | 7/2008 | Brown |
| 2012/0043482 | A1* | 2/2012 | Prince .................. A61N 5/1045 250/505.1 |
| 2013/0142313 | A1* | 6/2013 | Haider .................... G21K 1/02 378/150 |
| 2014/0112453 | A1 | 4/2014 | Prince et al. |
| 2016/0206899 | A1 | 7/2016 | Takahashi et al. |

FOREIGN PATENT DOCUMENTS

| | | |
|---|---|---|
| CN | 201233444 Y | 5/2009 |
| CN | 203767096 U | 8/2014 |
| CN | 204910511 U | 12/2015 |
| CN | 205031757 U | 2/2016 |
| CN | 207152891 U | 3/2018 |
| CN | 109224318 A | 1/2019 |
| EP | 0905714 A2 | 3/1999 |
| EP | 2687259 A1 | 1/2014 |
| EP | 2542306 B1 | 5/2018 |
| JP | H11216197 A | 8/1999 |
| JP | 2002065876 A | 3/2002 |

* cited by examiner

MULTI-LEAF COLLIMATOR AND RADIATION THERAPY DEVICE

CROSS-REFERENCE TO RELATED APPLICATIONS

This application claims priority to Chinese Application No. 201910407804.6, filed on May 15, 2019, the entire contents of which are hereby incorporated by reference.

TECHNICAL FIELD

The present disclosure generally relates to radiation therapy (RT) systems and methods, and more particularly, relates to a multi-leaf collimator of a radiation device and methods using thereof.

BACKGROUND

Radiation therapy is a common method for treating diseases such as malignant tumor. A multi-leaf collimator (MLC) is an important device for precise radiation therapy. The MLC may include a plurality of leaves used for allowing selective passage of radiation beams while blocking radiation beams that impinge on the plurality of leaves. Basic working principles for the MLC may include using a driving device to drive one or more leaves to move to a preset position so that the plurality of leaves can form an aperture of a desired shape. Thus, the radiation beams passing through the aperture form a therapeutic radiation field that conforms to the shape of a part of a subject (e.g., a tumor) to be irradiated.

For example, in radiotherapy, radiation beams such as X-rays pass through a primary collimator and a secondary collimator to form conical beams that can be projected onto an isocentric plane to obtain a preliminary radiation field (such as a circular radiation field). The X-rays further pass through an adjustable MLC to form a suitable therapeutic radiation field on the isocentric plane. In existing MLCs, the length of leaves of an MLC are generally the same. But in practical usage of such MLCs, there can be a portion of at least one leaf where no radiation beams may reach. Thus, it is desired to provide an MLC of an improved design that takes less materials and reduced manufacturing cost.

SUMMARY

According to an aspect of the present disclosure, a multi-leaf collimator is provided. The multi-leaf collimator may include a set of leaves installed in a cavity, each leaf of the set of leaves having a length along a first direction. At least a portion of the set of leaves may extend beyond the cavity along the first direction. The set of leaves may be arranged along a second direction, the second direction being different from the first direction. A length of a target leaf of the set of leaves may be less than a length of a reference leaf of the set of leaves. The target leaf may be located in an end portion of the set of leaves along the second direction.

In some embodiments, the set of leaves may include a plurality of target leaves located at both end portions of the set of leaves along the second direction.

In some embodiments, the set of leaves may include a group of reference leaves of a same length and a plurality of target leaves located on both sides along the second direction of the group of reference leaves. Lengths of at least two of the plurality of target leaves may be different from each other.

In some embodiments, the lengths of the at least two of the plurality of target leaves may gradually increase or decrease along the second direction.

In some embodiments, the multi-leaf collimator may further include a box. The cavity may be within the box, and a dimension of at least one end portion of the box may be less than a dimension of a middle portion of the box.

In some embodiments, each leaf of the set of leaves may be located in a leaf plane, and a plurality of leaf planes intersect substantially at a focus point.

In some embodiments, the multi-leaf collimator may further include a second set of leaves installed in a second cavity. Each leaf of the second set of leaves having a length along a first direction, at least a portion of the second set of leaves extending beyond the second cavity along the first direction. The second set of leaves may be arranged along the second direction. A length of a second target leaf of the second set of leaves may be less than a length of a second reference leaf of the second set of leaves. The second target leaf may be located in an end portion of the second set of leaves along the second direction. The set of leaves may be disposed in a first plane, and the second set of leaves may be disposed in a second plane, the second plane being different from the first plane.

In some embodiments, the second set of leaves may include a plurality of second target leaves located in both end portions of the second set of leaves along the second direction.

In some embodiments, the lengths of the at least two of the plurality of second target leaves may gradually increase or decrease along the second direction.

In some embodiments, the second set of leaves may include a group of second reference leaves of a same length, and a plurality of second target leaves located on both sides along the second direction of the group of second reference leaves. Lengths of at least two of the plurality of second target leaves may be different from each other.

In some embodiments, the multi-leaf collimator may further include a second box. The second cavity may be within the second box, and a dimension of at least one end portion of the second box may be less than a dimension of a middle portion of the second box.

In some embodiments, the set of leaves and the second set of leaves may be staggered such that radiation that leaks through an inter-leaf space between a pair of neighboring leaves of at least some of the set of leaves may be at least partially blocked by a leaf of the second set of leaves.

In some embodiments, each leaf of the second set of leaves may be located in a second leaf plane, and a plurality of second leaf planes intersect substantially at a second focus point.

In some embodiments, a width of each of at least some of the set of leaves projected onto a third plane may be the same as a width of each of at least some of the second set of leaves projected onto the third plane, wherein the third plan may be parallel to the first direction and the second direction.

According to another aspect of the present disclosure, a radiation therapy (RT) device including a multi-leaf collimator is provided. The multi-leaf collimator may include a set of leaves installed in a cavity. Each leaf of the set of leaves may have a length along a first direction. At least a portion of the set of leaves may extend beyond the cavity along a first direction, wherein the set of leaves may be arranged along a second direction. The second direction may be different from the first direction. A length of a target leaf of the set of leaves may be less than a length of a reference leaf of the set of leaves. The target leaf may be located in an end portion of the set of leaves along the second direction.

In some embodiments, the multi-leaf collimator may include a second set of leaves installed in a second cavity, each leaf of the second set of leaves having a length along the first direction. At least a portion of the second set of leaves may extend beyond the second cavity along the first direction. The second set of leaves may be arranged along the second direction. A length of a second target leaf of the second set of leaves may be less than a length of a second reference leaf of the second set of leaves. The second target leaf may be located in an end portion of the second set of leaves along the second direction. The set of leaves may be disposed in a first plane, and the second set of leaves may be disposed in a second plane, the second plane being different from the first plane.

In some embodiments, the multi-leaf collimator may include a first pair of boxes that are symmetrically disposed with respect to the second direction. Each of the first pair of boxes may include the cavity where the set of leaves may be located. The multi-leaf collimator may include a second pair of boxes that are symmetrically disposed with respect to the second direction. Each of the second pair of boxes may include the second cavity where the second set of leaves may be located, and each leaf of the sets of leaves and the second sets of leaves may be movable along the first direction. Each box of the first pair of boxes and the second pair of boxes may be movable along the first direction.

In some embodiments, a width of each of at least some of the set of leaves projected onto a third plane may be the same as a width of each of at least some of the second set of leaves projected onto the third plane, the third plane being an isocentric plane.

In some embodiments, the set of leaves may include a group of reference leaves of a same length, and a plurality of target leaves located on both sides along the second direction of the group of reference leaves. Lengths of at least two of the plurality of target leaves may be different from each other.

In some embodiments, the lengths of the at least two of the plurality of target leaves gradually increase or decrease along the second direction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
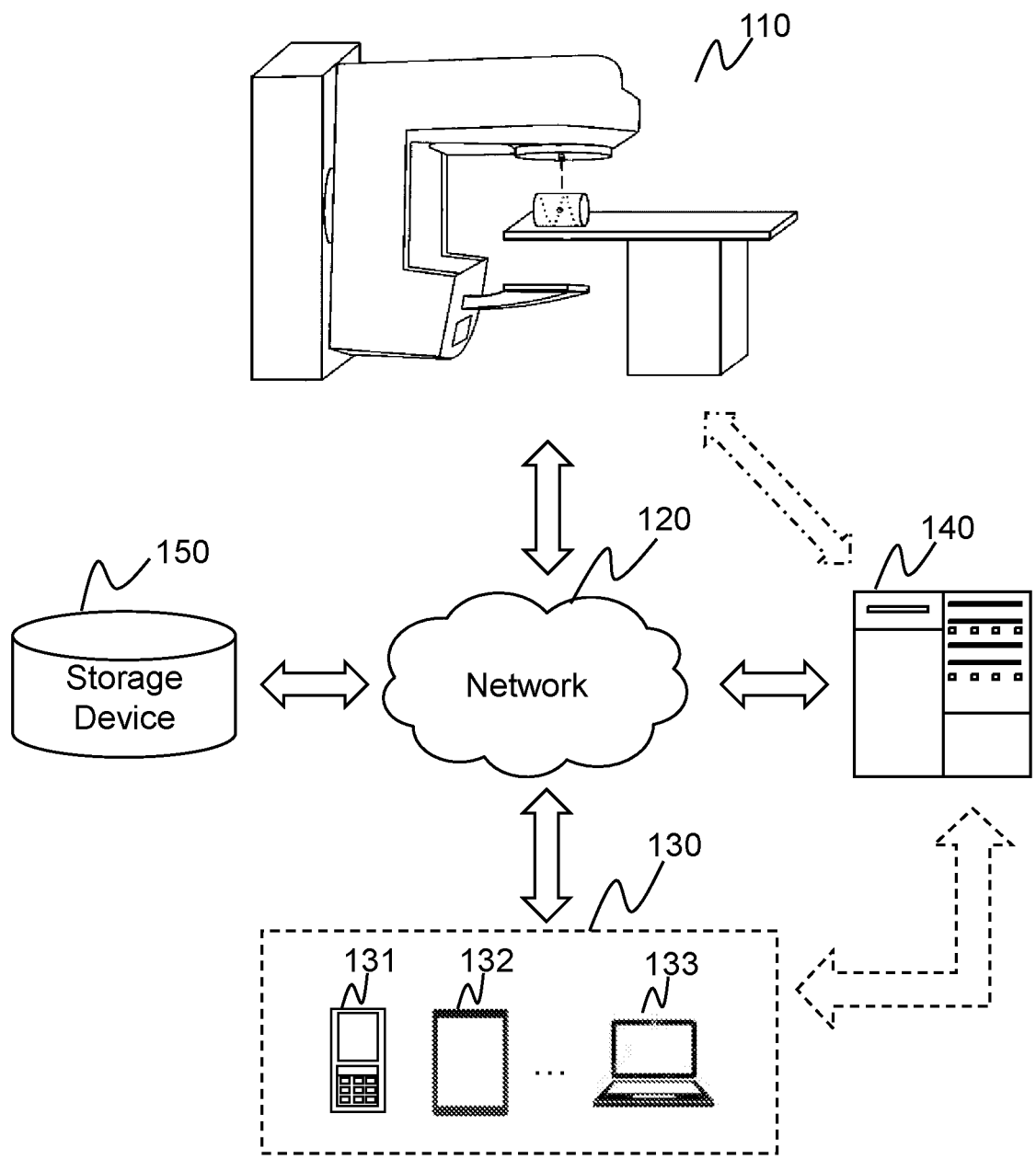
FIG. 1 is a schematic diagram illustrating an exemplary RT system according to some embodiments of the present disclosure.

In order to illustrate the technical solutions related to the embodiments of the present disclosure, brief introduction of the drawings associated with the embodiments is provided below. Obviously, drawings described below are only some examples or embodiments of the present disclosure. Those having ordinary skills in the art may apply the present disclosure to other similar scenarios according to these drawings without further creative efforts. Unless obviously obtained from the context or the context illustrates otherwise, the same numeral in the drawings refers to the same structure or process.

As used in the disclosure and the appended claims, the singular forms "a," "an," and "the" include plural referents unless the content clearly dictates otherwise. In general, the terms "comprise" and "include" merely prompt to include steps and elements that have been clearly identified, and these steps and elements do not constitute an exclusive listing. The methods or devices may also include other steps or elements.

The present disclosure describes various means for implementation of MLC. It should be understood that the present disclosure is not limited to the specific embodiments described herein, and may be modified, modified, and/or changed. The solution described in connection with a specific embodiment is not necessarily limited to this embodiment and can be implemented in any other solution. For example, while various embodiments have been described in connection with a radiotherapy device, it should be understood that the present disclosure can also be implemented in other electromagnetic devices and modalities. It is also understood that the terminology used herein is for the purpose of describing the particular embodiments, and the scope of the present disclosure is defined by the scope of the appended claims. Further, various embodiments are described with reference to the drawings. It should be noted that the figures are not drawn to scale and are merely intended to facilitate the description of the specific embodiments. The drawings are not intended to be exhaustive or to limit the scope of the present disclosure.

In order to facilitate the description of the relative position, orientation or spatial relationship in conjunction with the drawings, various relative terms such as "top", "above", "on top of", "directly above", "on", "below", "underneath", "bottom", "higher", "lower" or similar terms may be used herein. For example, when the source of radiation is above the isocentric plane and the MLC is between them, the term "level" or "upper level" may be used for ease of describing some embodiments. The use of the relative terms should not be construed as implying the orientation, position, or direction of the structure or portions thereof as necessary for the manufacture or use, and should not be construed as limiting the scope of the present disclosure. As used in the specification and the appended claims, unless the context clearly indicates, otherwise, the singular forms "a", "an", and "said" may include a plurality of referents. For example, reference to "direction" may include the opposite direction of the direction and the a plurality of directions parallel to the direction.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure provides a multi-leaf collimator (MLC) for limiting the range of radiation beams to conform to the shape of a part of a subject (e.g., a portion of the lung of a patient) to be irradiated. The MLC may include a set of leaves installed in a cavity, which are movable along a first direction to form an aperture that allows radiation beams to pass through. The length of at least a portion of the set of leaves may be different from another portion of the set of leaves, which can conform to the shape of a maximum therapeutic radiation field (i.e., a radiation field that is not blocked by any leaf in the MLC, also referred to as a "preliminary radiation field") projected onto an isocentric plane of a radiotherapy device. Thus, the materials and the cost for manufacturing the set of leaves may be reduced. Leaves of reduced weight may be maneuvered more easily with improved precision, which in turn may reduce the complexity and/or cost of the driving components of the MLC. The length of the at least a portion of the set of leaves may be determined according to the shape of the maximum therapeutic radiation field. For example, for a maximum therapeutic radiation field having the shape of a circle, the lengths of at least a portion of the set of leaves may gradually change (e.g., increase, decrease) along a second direction in which the set of leaves are arranged. The shape of a box where the set of leaves are housed and installed may also be designed according to the lengths of the set of leaves. For instance, at least a portion of the box may include a cambered surface. Compared to a box with a uniform dimension along the first direction in which the set of leaves are configured to move, the materials and cost for manufacturing a box of a non-uniform dimension that conforms to the shape of the set of leaves may be reduced. Additionally or alternatively, the box may be movable along the first direction, and the box and the set of leaves can move simultaneously, which may reduce a moving distance of one or more of the set of leaves with respect to the box. Thus, the time needed to form a desired therapeutic radiation field may be reduced, which in turn may result in reduced time for performing a radiotherapy treatment of the subject.

The MLC provided in the present disclosure may include boxes and leaves located in different planes. For example, in an upper plane, the MLC may include a first pair of boxes that are symmetrically disposed with respect to the second direction. Each of the first pair of boxes includes a cavity where a set of leaves are installed. In a lower plane, the MLC may include a second pair of boxes that are symmetrically disposed with respect to the second direction. Each of the second pair of boxes includes a second cavity where a second set of leaves are located. The first sets of leaves and the second sets of leaves may be arranged in a staggered manner such that radiation that leaks through an inter-leaf space between a pair of neighboring leaves of at least some of the first set of leaves is at least partially blocked by a leaf of the second set of leaves. Such an arrangement may also increase the resolution of the radiation field on the boundary of the radiation field.

The present disclosure further provides an RT device including the MLC described above and methods of using the same.

It should be noted that different embodiments may have different beneficial effects. In different embodiments, the beneficial effects that may be produced may be any combination of one or more of the above and may be any other beneficial effects that may be obtained.

FIG. 1 is a schematic diagram illustrating an exemplary RT system according to some embodiments of the present disclosure. As shown, the radiation therapy (RT) system 100 may include an RT device 110, a network 120, one or more terminals 130, a processing device 140, and a storage device 150. In some embodiments, the RT device 110, the terminal(s) 130, the processing device 140, and/or the storage device 150 may be connected to and/or communicate with each other via a wireless connection (e.g., the network 120), a wired connection, or a combination thereof. The connection between the components of the RT system 100 may be variable. Merely by way of example, the RT device 110 may be connected to the processing device 140 through the network 120, as illustrated in FIG. 1. As another example, the RT device 110 may be connected to the processing device 140 directly. As a further example, the storage device 150 may be connected to the processing device 140 through the network 120, as illustrated in FIG. 1, or connected to the processing device 140 directly. As still a further example, a terminal 130 may be connected to the processing device 140 through the network 120, as illustrated in FIG. 1, or connected to the processing device 140 directly.

The RT device 110 may deliver a treatment plan to a subject (e.g., a patient) on a couch of the RT device 110. In some embodiments, the RT device 110 may be a multi-modality (e.g., two-modality) apparatus to acquire a medical image and perform radio therapy. The medical image may be a Computed Tomography (CT) image, a Magnetic Resonance (MR) image, an ultrasonic image, a four-dimensional (4D) image, a three-dimensional (3D) image, a two-dimensional (2D) image, a diagnostic image, and a non-diagnostic image, or the like, or a combination thereof. The RT device 110 may include one or more imaging devices and/or treatment devices. For example, a CT device, a Cone beam CT, a Positron Emission Tomography (PET), a Volume CT, an MRI device, an RT device, or the like, or a combination thereof. In some embodiments, the imaging device(s) may acquire an image of the subject prior to an RT treatment, during an RT treatment and/or after an RT treatment. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or ROI, such as an esophagus, a trachea, a bronchus, a stomach, a gallbladder, a small intestine, a colon, a bladder, a ureter, a uterus, a fallopian tube, etc.

The network 120 may include any suitable network that can facilitate exchange of information and/or data for the RT system 100. In some embodiments, one or more components of the RT system 100 (e.g., the RT device 110, the processing device 140, the storage device 150, the terminal(s) 130) may communicate information and/or data with one or more other components of the RT system 100 via the network 120. For example, the processing device 140 may obtain image data from the RT device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

The terminal(s) 130 may be connected to and/or communicate with the RT device 110, the processing device 140, and/or the storage device 150. For example, the terminal(s) 130 may obtain a processed image from the processing device 140. As another example, an operator may send an instruction to the one or more components of the RT system 100 via the terminal(s). In some embodiments, the terminal (s) 130 may include a mobile device 131, a tablet computer 132, a laptop computer 133, or the like, or any combination thereof. For example, the mobile device 131 may include a mobile phone, a personal digital assistance (PDA), a gaming device, a navigation device, a point of sale (POS) device, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 130 may be part of the processing device 140.

The processing device 140 may process data and/or information obtained from the RT device 110, the storage device 150, the terminal(s) 130, or other components of the RT system 100. For example, the processing device 140 may generate controlling signals for controlling the movement of one or more leaves in the MLC of the RT device 110 to achieve a suitable therapeutic radiation field. As another example, the processing device 140 may generate an RT treatment plan by optimizing relevant parameters, such as parameters associated the movement of the one or more leaves in the MLC. In some embodiments, the processing device 140 may be a single server or a server group. The server group may be centralized or distributed. In some embodiments, the processing device 140 may be local to or remote from the RT system 100. For example, the processing device 140 may access information and/or data from the RT device 110, the storage device 150, and/or the terminal(s) 130 via the network 120. As another example, the processing device 140 may be directly connected to the RT device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a mobile device 300 having one or more components as described in connection with FIG. 3.

The storage device 150 may store data, instructions, and/or any other information. In some embodiments, the storage device 150 may store data obtained from the RT device 110, the terminal(s) 130, and/or the processing device 140. In some embodiments, the storage device 150 may store data and/or instructions that the processing device 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the RT system 100 (e.g., the processing device 140, the terminal(s) 130). One or more components of the RT system 100 may access the data or instructions stored in the storage device 150 via the network 120. In some embodiments, the storage device 150 may be part of the processing device 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

Figure 2:
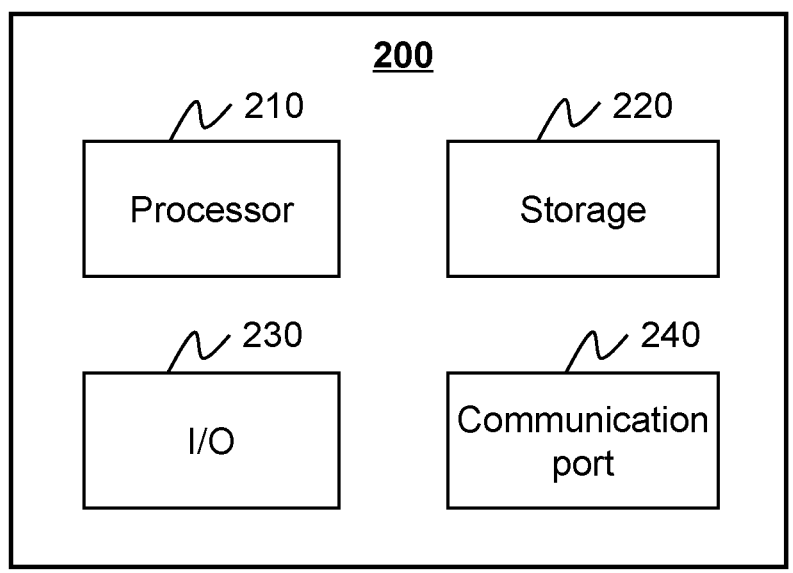
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240. In some embodiments, the computing device 200 may generate an RT plan for delivering radiation to a subject. For example, the RT plan may include moving parameters for a plurality of leaves in the MLC of the RT device 110.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may send controlling signals to the RT device 110, the terminals 130, the storage device 150, and/or any other component of the RT system 100. Merely by way of example, the processor 210 may generate controlling signals for controlling the movement of one or more leaves in the MLC of the RT device 110 to achieve a suitable therapeutic radiation field. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation s A and B).

The storage 220 may store data/information obtained from the RT device 110, the terminals 130, the storage device 150, and/or any other component of the RT system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining the position of a target region of a subject (e.g., a target portion of a patient).

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the RT device 110, the terminals 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
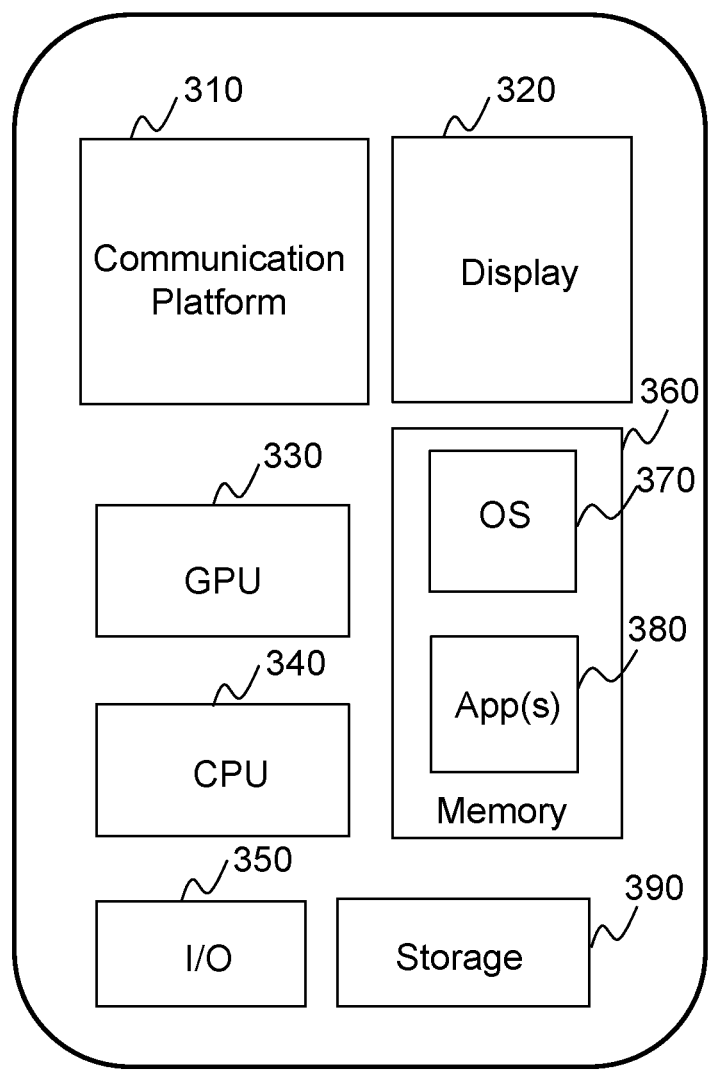
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminals 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to an RT plan or other information from the processing device 140. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
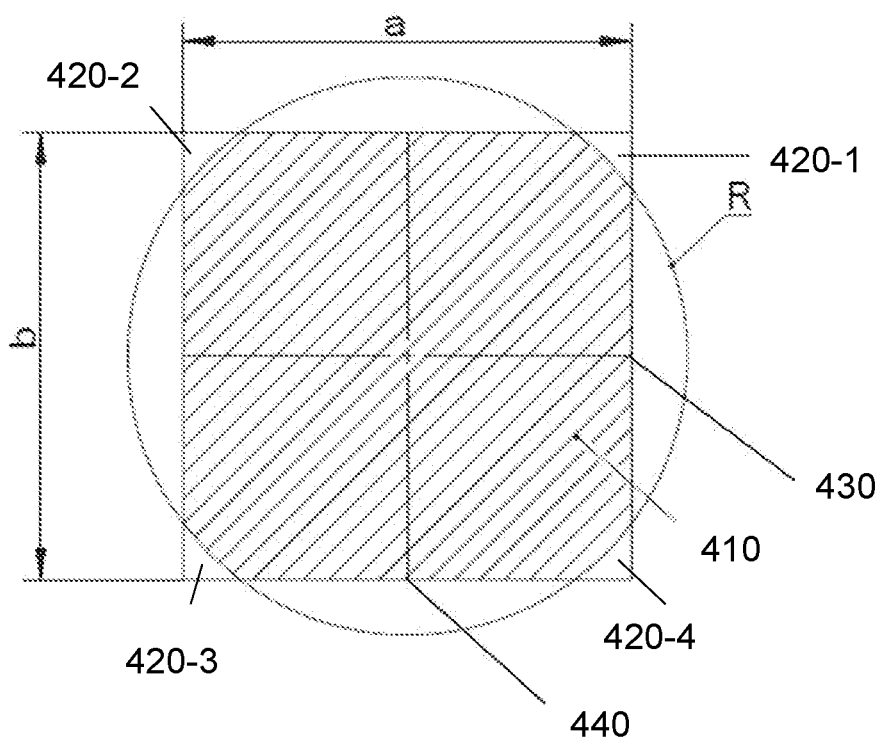
FIG. 4 is a schematic diagram illustrating an exemplary maximum radiation field according to some embodiments of the present disclosure.

FIG. 4 is a schematic diagram illustrating an exemplary maximum radiation field according to some embodiments of the present disclosure. For illustrative purposes only, the formation of the radiation field is described below. In a process of radiation therapy (RT), radiation beams (e.g., X-rays) emitted from a radiation source (e.g., an X-ray source) may pass through devices, such as one or more collimators, an MLC, and may be projected onto an isocentric plane to form a therapeutic radiation field. The therapeutic radiation field may indicate a range of the radiation beams that are delivered to the subject. The isocentric plane may be a plane that is perpendicular to the main optical axis of the radiation beams that pass through the isocenter of the RT device. The intersection of the main optical axis of the radiation beams and the isocentric plane is an isocenter. The one or more collimators may include a primary collimator and an optional secondary collimator (such as a tungsten gate), which may be used to determine a substantially limited range of the radiation beams after the radiation beams are emitted from the source. In some embodiments, the therapeutic radiation field may be a portion of the preliminary radiation field or the whole preliminary radiation field. The MLC may be disposed between the radiation source and the isocentric plane for further adjusting or defining the shape and/or intensity of the radiation beams emitted onto the isocentric plane. In some embodiments, the collimator(s) and/or the MLC may include a portion thereof for blocking radiation beams, which can be made of a radiation shielding material including, e.g., lead, tungsten, or the like, or a combination thereof. In some embodiments, the collimator and/or the MLC may form a through-hole or aperture of a specific shape, through which radiation beams can pass. In some embodiments, a portion of the radiation beams may be blocked by a portion of the collimator and/or the MLC (such as one or more leaves of the MLC).

In some embodiments, a conical through-hole may be formed on the primary collimator. When the radiation beams emitted from the radiation source reaches the primary collimator, at least a portion of the radiation beams may pass through the conical through-hole. In some embodiments, another portion of the radiation beams that impinge on other parts of the primary collimator (e.g., one or more leaves of the primary collimator) may be blocked, shielded, and/or absorbed, thereby not passing through the primary collimator. The radiation beams passing through the conical through-holes may form cone beams. If the cone beams do not traverse other beam-limiting components, such as a secondary collimator and/or MLC, the cone beams may form a circular radiation field on the isocentric plane. After the primary collimator (e.g., below the primary collimator), there may be a secondary collimator that further defines the radiation beams that have passed through the primary collimator. In general, the secondary collimator may have or form a beam limiting aperture, such as a rectangular aperture. Similarly, when the radiation beams reach the secondary collimator, at least a portion of the radiation beams may pass through the beam limiting aperture. In some embodiments, another portion of the radiation beams that impinge on other parts of the secondary collimator may be blocked, shielded, and/or absorbed. The projection of the radiation beams that have passed through the secondary collimator on a plane (e.g., a plane parallel to the isocentric plane) may form a region referred to as the preliminary radiation field, that is, the maximum region that the radiation beams coming out of the secondary collimator can occupy. It may be understood that the plane may also be a plane where the MLC is mounted in.

The MLC can form a variety of regularly or irregularly shaped aperture that conform to the shape of a part of a subject (e.g., a portion of the heart, a portion of the lung of a patient) to be treated by the control device. After passing through the primary collimator, a portion of X-rays may be shielded by the MLC (e.g., by a plurality of leaves that can block the X-rays). Another portion of the X-rays may pass through the regularly or irregularly shaped aperture formed by the MLC and reach the part of the subject that needs treatment. FIG. 4 is provided in order to better illustrate the formation of the radiation beams.

As shown in FIG. 4, radiation beams emitted by a radiation source may form cone-shaped radiation beams after passing through the primary collimator. If there are no other beam-limiting components after the primary collimator (e.g., below the primary collimator), the cone beams may be projected onto the isocentric plane to form a circular radiation field of radius R. The value of R may depend on the size of the conical aperture of the primary collimator and a distance between the primary collimator and the isocentric plane. After passing through the primary collimator, the cone beams may pass through a secondary collimator. It is understood that the radiation beams projected on the mounting plane of the secondary collimator may also be a circle. For the purpose of limiting the radiation beams, a rectangular aperture provided or formed in the secondary collimator may further limit the range of the radiation beams. That is, a portion of the cone beam may be blocked and not projected onto the isocentric plane. It should be noted that after passing through the secondary collimator, the preliminary radiation field may have a desired shape, such as a rectangle, a trapezoid, a trapezoidal trapezoid, a parallelogram, or the like. The length of the at least a portion of the set of leaves may be determined according to the shape of the preliminary radiation field.

Referring to FIG. 4, the projection region of the radiation beams on the isocentric plane after passing through the secondary collimator is limited to a rectangular range of a×b. The dimensions of a and b may depend on the length and width of the rectangular aperture and the distance between the secondary collimator and the isocentric plane. In FIG. 4, a shadow region 410 refers to a radiation field (i.e., the primary radiation filed) formed by the radiation beams in the isocentric plane after passing through the primary collimator and the secondary collimator. The shadow region 410 may also be the largest radiation field that the radiation beams can occupy. Regions 420-1, 420-2, 420-3, 420-4 shown in FIG. 4 are blank regions, which may be collectively referred to as a region 420. No radiation beams emitted from the radiation source may pass through the region 420. It should be understood that although the rectangular aperture of the secondary collimator allows radiation beams to pass through the four vertex regions (e.g., the region 420) of the aperture, no radiation beams that have passed through the primary collimator are projected onto the four apex regions. Therefore, in the isocentric plane, a blank region 420 as shown in FIG. 4 is formed. Line 430 is the first centerline of the radiation field 410, and line 440 is the second centerline of the radiation field 410. The centerlines pass through the isocenter of the isocentric plane and are perpendicular to each other. In the present disclosure, the first centerline may also be referred to as the horizontal axis, and the second centerline may also be referred to as the vertical axis. It should be appreciated that there may be a plurality of planes parallel to the isocentric plane that are located between the isocentric plane and the secondary collimator. The radiation beams may be projected onto at least one of the plurality of planes parallel to the isocentric plane to form a radiation field of the same shape but different size as compared to the radiation field 410. The center point of these radiation fields is located on the main optical axis of the radiation beams. The main optical axis of the radiation beams may be the axis of the line between the radiation source and the isocenter. In any of the radiation fields, there may be two centerlines perpendicular to each other and both pass through a center point of the radiation field. For example, the two centerlines correspond to the first centerline 430 and the second centerline 440 as shown in FIG. 4.

The MLC may be mounted in one of the plurality of planes parallel to the isocentric plane for further modulating the radiation beams. The MLC may include a plurality of pairs of leaves. Each pair of leaves may be symmetrically disposed on either side of the radiation field in the plane. For example, each pair of leaves may be symmetrically disposed with respect to the centerline of the radiation field. Leaves on the same side of may be arranged adjacently. For example, the leaves may be arranged along the same direction, and each of the leaves is adjacent to another leaf of the leaves. Each leaf of the MLC may be moved independently, for example, towards the interior of the radiation field or away from the radiation field. When each of the leaves is located at a pre-set position, a specific shape of the aperture may be obtained. After the radiation beams pass through the aperture, the radiation beams may be projected on the isocentric plane to obtain a corresponding radiation field (i.e., the therapeutic radiation field). In the prior art, an MLC is designed such that the maximum beam limiting range of the leaves covers not only the maximum radiation field 410 formed by the radiation beams in the plane, but also blank region(s) where no radiation beams may pass through (e.g., the blank region 420).

Therefore, a new design of the MLC leaves is provided. Rather than leaves of the same length in a box, the lengths of a portion of leaves located in both end portions of the arranged leaves (perpendicular to the direction of motion of the leaves) in the box vary (e.g., shortened or prolonged) according to the shape of the maximum radiation field (i.e., the primary radiation field) to reduce the materials and cost for manufacturing the MLC leaves.

Figure 5:
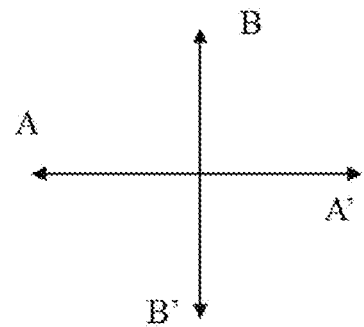
FIG. 5 is a schematic diagram illustrating a structure of an exemplary MLC according to some embodiments of the present disclosure.
Figure 5:
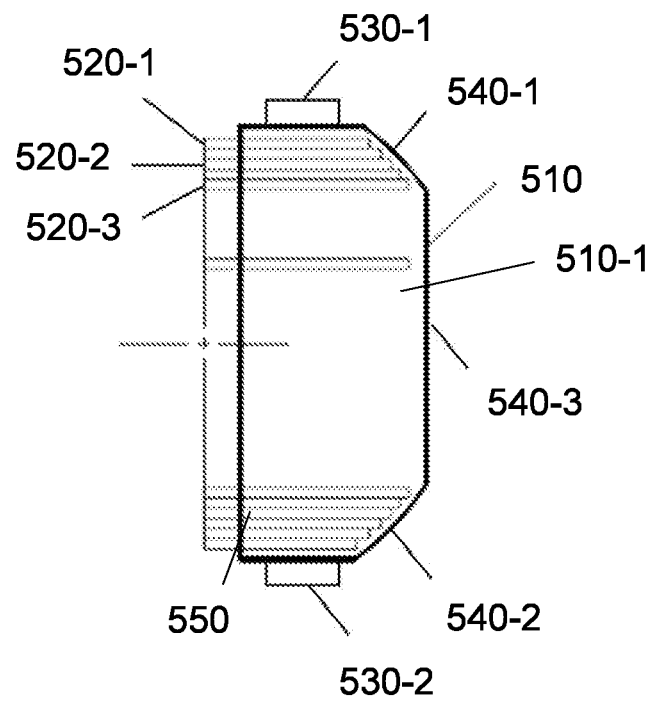

FIG. 5 is a schematic diagram illustrating the structure of an exemplary MLC according to some embodiments of the present disclosure. As shown in FIG. 5, the MLC may include the first box (or box for brevity) 510. The first box 510 may have a first cavity 510-1. The first cavity 510-1 may be a cavity continuous in a first direction in the MLC. As an example, the AA' line shown in FIG. 5 may be used to indicate the first direction. The first cavity 510-1 may be used to house and support other components of the MLC, such as leaves. In some embodiments, the shape of the first box 510 may be similar to a cuboid. The first box 510 may be made of lead, aluminum, tungsten, or other materials having radiation shielding capability, or an alloy thereof. Thus, the first box 510 may, to a certain extent, act to absorb leaked radiation beams. Since the shielding of a portion of the radiation beams is mainly achieved by the leaves of the MLC, the first box 510 may also be made of a material that does not have the ability to shield radiation beams, for example, steel. In some embodiments, a portion of the first box 510 may be made of a material having a radiation shielding capability, and a portion made of a material having no radiation shielding capability, and thus such first box 510 may adapt to various application needs for the MLC.

In the present disclosure, the MLC box may be described using the following terms. An "end" of the box used herein may refer to the two surfaces of the first cavity of the box. The "top and bottom" faces of the box may refer to the two surfaces of the box that are parallel to a plane along AA' (e.g., a plane parallel to the first direction) and a plane along BB' (e.g., a vertical plane), and may also refer to two surfaces parallel to the isocentric plane when the box is installed in an RT device. The top face may be closer to the radiation source thans the bottom face. The "side" faces of the box may refer to two surfaces on the box that are parallel to the first direction (such as the AA' linear direction). For example, a side face of the box may be perpendicular to the top and/or bottom faces of the box. In some embodiments, both sides of the first box 510 may be provided with first connecting components 530-1 and 530-2. The first connecting components 530-1 and 530-2 may be disposed on the first box 510 by means such as welding, riveting, screwing, bonding, or the like. Through the first connecting components 530-1 and 530-2, the first box 510 may be installed in an RT device to limit the range of the radiation beams.

As shown in FIG. 5, the MLC may include a first set of leaves. The first set of leaves may include a plurality of leaves, for example, leaf 520-1, leaf 520-2, leaf 520-3, . . . , leaf 520-$n$, where n may be a positive integer greater than one. The first set of leaves may be installed in the first cavity 510-1 of the first box 510. For example, the first cavity 510-1 is provided with a plurality of grooves for the leaves, and each leaf is mounted in its corresponding groove. In some embodiments, a plurality of leaves in the first set of leaves are arranged in a second direction within the first cavity 510-1. In some embodiments, the second direction may be different from the first direction (e.g., perpendicular to the first direction). As an example, the BB' line shown in FIG. 5 may be used to indicate the second direction. In some embodiments, the lengths of at least a portion of the first set of leaves may be the same and/or different. In the present disclosure, the "length" of a leaf may refer to the dimension of the leaf in the first direction. The "width" of the leaf may refer to the dimension of the leaf in the second direction. The "height" of a leaf may refer to the dimension of the leaf in the direction of the radiation beams when the leaf is mounted in an RT device.

In some embodiments, the length of the at least a portion of the set of leaves may be determined according to the shape of the maximum therapeutic radiation field. In some embodiments, the length of at least one of the leaves of the first set of leaves (also referred to as a target leaf) located at one end portion or both end portions of the first set of leaves in the second direction is different from the length of some other leaves (also referred to as reference leaves). The reference leaves may be located in a middle portion of the first set of leaves. The reference leaves may have a same length. In some embodiments, the length of at least one of the target leaves of the first set of leaves may be less than the length of the reference leaves. In conjunction with the description of FIG. 4, when the leaves are used to modulate the radiation beams, at least one leaf located at the end potion(s) in the second direction does not need to cover the blank region 420. Thus, at least one of the target leaves may be designed to be shorter than some other leaves, for example, less than the length of the leaf for covering the radiation field near the first centerline 430 (a reference leaf). The lengths of a portion of the leaves that do not cover the blank region 420 when conforming to the radiation beams (e.g., reference leaves) may be uniform. As shown in FIG. 4, in the second direction, the closer to the first centerline 430, the smaller the range of the blank region 420 is. Therefore, the range of coverage by the leaf is greater. In some embodiments, the first set of leaves may include a plurality of leaves of an equal length in the first direction. When the position(s) of one or more leaves is adjusted for limiting the range of the radiation beams, leaves of the equal length do not need to traverse the blank region 420 during modulation and the leaves need to cover the same range, so the lengths of the reference leaves may be set to be the same. In the second direction, on both sides of the plurality of equal-length leaves (i.e., the reference leaves), the first set of leaves include one or more leaves of unequal lengths (i.e., the target leaves). In some embodiments, the lengths of the leaves of unequal lengths may gradually increase or decrease along the second direction. The lengths of the target leaves at the farthest end of the both end portions in the second direction may be the shortest among the first set of leaves. The lengths of the target leaves may gradually increase along the second direction toward the middle portion of the first cavity 510-1 until the length of a target leaf is the same as the length of a reference leaf. Or it should be understood that on both sides of the reference leaves of an equal length, the lengths of the target leaves may gradually decrease along the second direction away from the middle portion of the first cavity 510-1. For example, as shown in FIG. 5, the length of the leaf 520-1 is the smallest. The length of the leaf 520-2 near the middle portion of the box is greater than the length of the leaf 520-1. The length of the leaf 520-3 that does not need to traverse the blank region 420 when being moved to limit the range of radiation beams is the longest among the first set of leaves and is also the same as the length of some other leaves.

In some embodiments, the leaves mounted in the first cavity 510-1 may partially extend out of the first cavity 510-1. Therefore, the shape of the first box 510 may be adapted according to the plurality of leaves of the first set of leaves installed therein. In some embodiments, the size of the first box 510 in the first direction may vary. The portions inside the first cavity 510-1 adjacent to both sides of the first box 510 is for mounting and supporting the shorter leaves. Therefore, the dimension of the portion of the first box 510 corresponding to the portions of the first cavity 510-1 where shorter leaves are mounted may be smaller than the dimension of the middle portion of the box. This may not only allow the installation and support of the leaves, but also stable movements of the leaves, and further reducing the manufacturing cost of the box. In some embodiments, the dimension of the first box 510 in the first direction gradually increases toward the middle portion of the box. In some embodiments, at least one of the end faces of the first box 510 is composed of at least two sections. Merely by way of example, the at least two sections may include a first section and a second section. A distance between the first section and the other end face (e.g., the end face 550 shown in FIG. 5) of the first box 510 is different from a distance between the second section and the other end face of the first box 510. As an example, as shown in FIG. 5, one end surface of the first box 510 includes first sections 540-1 and 540-2 and a second section 540-3, and the first sections 540-1 and 540-2 are connected with the second section 540-3 and a side face (e.g., the side face 530-1, 530-2, respectively) of the first box 510. Moreover, the distance in the first direction between the first portions 540-1 and 540-2 and the other end surface of the first box 510 is less than the distance in the first direction between the second portion 540-3 and the other end surface. The distance between the first portions 540-1 and 540-2 and the other end face of the first box 510 in the first direction may gradually change along the second direction. For example, along the second direction, the closer to the end portion of the box 510, the smaller the distance between the first sections 540-1/540-2 and the other side in the first direction; the closer to the middle portion of the box 510, the greater the distance between the first portions 540-1/540-2 and the other side in the first direction; the middle portion of the box 510 may be composed of the second section 540-3 and a middle portion of the side face 550 in the first direction. The distance between the second section 540-3 and the middle portion remains constant. Optionally, the first sections 540-1 and 540-2 are smooth curved surfaces, for example, curved surfaces, such that the first sections 540-1 and 540-2 may also be referred to as curved sections. Optionally, the first sections 540-1 and 540-2 may include a series of planes. When the MLC is installed in an RT device, the first box may be mounted such that the curved sections 540-1 and 540-2 are on the side away from the central axis of the radiation beams, that is, the curved sections 540-1 and 540-2 may be located at positions corresponding to the edge of the radiation field. In some embodiments, the first box 510 may be of a shape that does not conform to the leaves, but maintaining a shape similar to a cuboidal.

Figure 6:
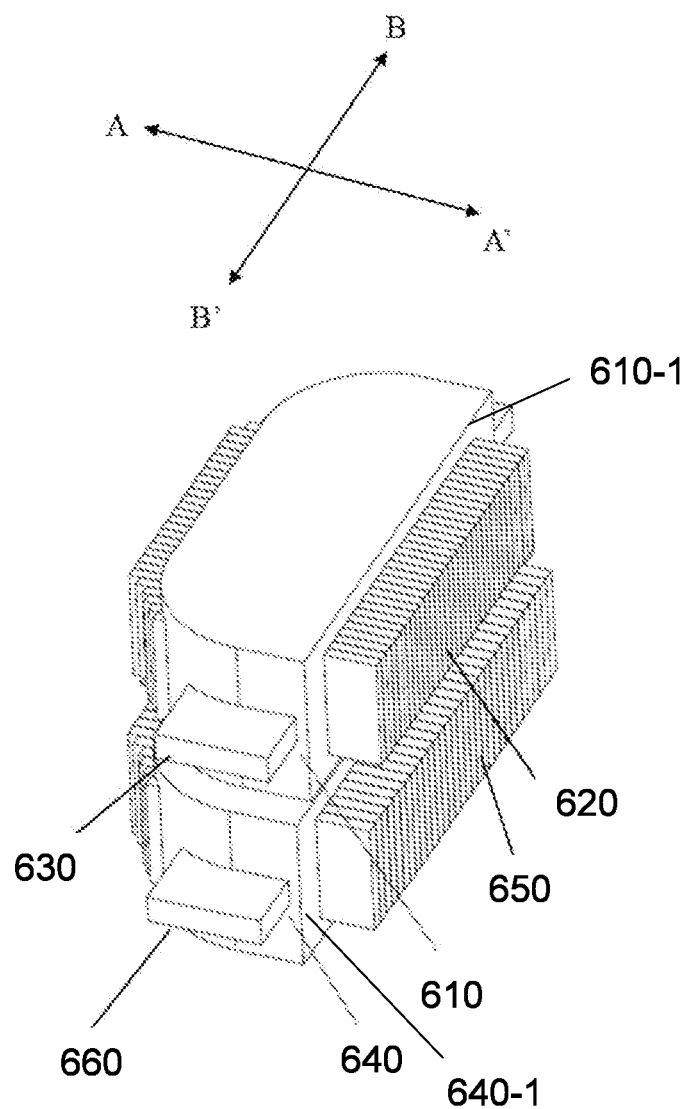
FIG. 6 is a schematic diagram illustrating a structure of an exemplary MLC according to some embodiments of the present disclosure.

FIG. 6 is a schematic diagram illustrating a structure of an exemplary MLC according to some embodiments of the present disclosure. As shown in FIG. 6, the MLC may include a first box 610 having a first cavity 610-1 that penetrate through the first box 610 in a first direction, a first set of leaves 620 including a plurality of leaves, and a first connecting component 630 disposed on both sides of the first box 610. A plurality of leaves are mounted in the first cavity 610-1 and at least a portion of the leaves extend beyond the first cavity 610-1. A description of the first box 610, the first set of leaves 620, and the first connecting component 630 may refer to the description of the first box 510, the first set of leaves, and the first connecting component 530-1/530-2 in FIG. 5, which is not repeated here.

In some embodiments, the MLC may include a pair of boxes disposed in only one plane. In some embodiments, the MLC may include two or more pairs of boxes disposed in two or more planes, respectively. In some embodiments, the MLC may further include a second box 640 having a second cavity 640-1 that penetrates through the second box 640 in the first direction, a second set of leaves 650 including a plurality of leaves, and a second connecting component 660 disposed on both sides of the second box 640. A plurality of leaves are mounted in the second cavity 640-1 and partially extend beyond the second cavity 640-1. The second box 640 may have a second cavity 640-1 that penetrates through the second box 640 in the first direction. As an example, the AA' direction shown in FIG. 6 may be used to indicate the first direction. The second cavity 640-1 may be used to house and support other components of the MLC, such as a second set of leaves. A second set of leaves 650 is mounted within the second cavity 640-1 and partially extends out of the second cavity 640-1. The second set of leaves 650 may include a plurality of leaves that are successively arranged in the second direction, and the number (or count) of leaves included may be the same as or different from the number of leaves included in the first set of leaves 620. As an example, the BB' direction shown in FIG. 6 may be used to indicate the second direction. As illustrated in FIG. 6, the second direction is perpendicular to the first direction. In the second set of leaves 650, the length of at least one leaf at the both ends in the second direction is less than the length of some other leaves. The number of leaves having a smaller length (i.e., the target leaves) included in the second set of leaves 650 may be the same as or different from the number of leaves having a smaller length (i.e., the reference leaves) included in the first set of leaves 620. The shape of the second box 640 may be similar to the first box 610 to adapt to the lengths of the leaves in the second set of leaves 650. Alternatively, the shape of the second box 640 may include a cuboid, a hexahedron, an octahedron, or the like.

The second box 640, the second set of leaves 650, and the second connecting component 660 may be similar to the first box 610, the first set of leaves 620, and the first connecting component 630, and accordingly the descriptions thereof are not repeated. The contents of other parts of the present disclosure (for example, FIG. 5) are available for reference. In some embodiments, second set of leaves 650 and first set of leaves 620 may be distributed in different planes. Merely by way of example, the first set of leaves 620 are distributed in the first plane Q, and the second set of leaves 650 may be distributed in the second plane P which is parallel to and below the first plane Q. In some embodiments, the second set of leaves 650 may be distributed below the first set of leaves 620. In some embodiments, the first set of leaves and the second set of leaves may be staggered such that radiation that leaks through an inter-leaf space between a pair of neighboring leaves of at least some of the first set of leaves is at least partially blocked by a leaf of the second set of leaves. As used herein, the term "staggered" refers to a manner of arranging the first set of leaves and the second set of leaves such that the position of each leaf from at least some of the second set of leaves is offset from a leaf of the first set of leaves. In some embodiments, the orthographic projection of a leaf of the first set of leaves 620 onto the second plane of the second set of leaves 650 may partially overlap each of a pair of two adjacent leaves in the second set of leaves 650. The leaves of the MLC may be movable. Therefore, the two adjacent leaves do not touch each other but have a certain gap (i.e., the inter-leaf space) to facilitate the movement of the leaves. However, the problem with the gap between the leaves (the inter-leaf space) is that there may be radiation leaking through the gap. Thus, by staggering the first set of leaves and the second set of leaves, radiation that leaks through an inter-leaf space between a pair of neighboring leaves of at least some of the first set of leaves is at least partially blocked by a leaf of the second set of leaves, thereby reducing the radiation leakage from the inter-leaf space(s). At the same time, the MLC leaves (first set of leaves 620 and second set of leaves 650) are designed to be placed in an upper plane and a lower plane, respectively, in a staggered manner, which may increase the resolution of the radiation field on the boundary of the radiation field. For example, at least a portion of the first set of leaves 620 may misalign with at least a portion of the second set of leaves by a distance, e.g., approximately a half of the width of a leaf, which is equivalent to limiting the range of radiation beams using relatively thin leaves.

Figure 8:
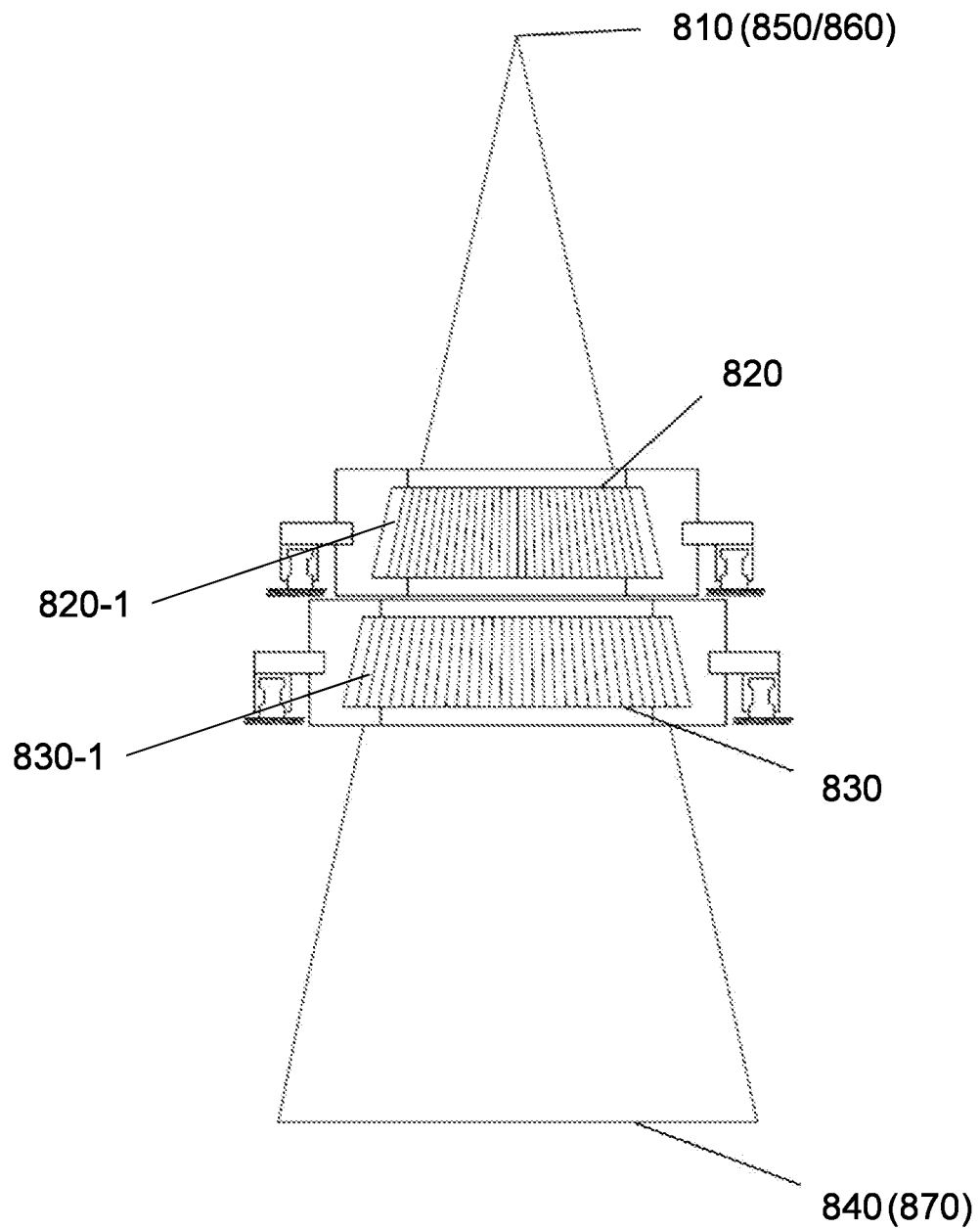
FIG. 8 is a side view of an exemplary MLC according to some embodiments of the present disclosure.

In some embodiments, the first set of leaves are arranged to be substantially focused onto a focus point (also referred to as a "first focus point," e.g., the first focus point 850 shown in FIG. 8). The arrangement may be referred to as a convergent arrangement. The focus point may be a virtual focus point substantially coinciding with the radiation source (e.g., the radiation source 810 shown in FIG. 8), which is understood to be the intersection of the leaf planes (e.g., the leaf planes 820-1 shown in FIG. 8) in which the leaves are located, respectively. In some embodiments, a plurality of leaf planes (e.g., the leaf planes 830-1 shown in FIG. 8) in which the second set of leaves are located intersect substantially at a second focus point (e.g., the second focus point 860 shown in FIG. 8), thereby constituting a convergent arrangement. In some embodiments, the second focus point may be substantially the same as the first focus point. The convergent arrangement may reduce the impact of the leaf side penumbra. Such an arrangement is intended to achieve an effect that there is substantially no overlap between the leaves when viewed from the radiation source, thereby increasing the conformal quality of the leaves at the isocenter. The widths of leaves from different sets of leaves in the MLC may be different. For example, the widths of the leaves that are closer to the radiation source may be less than the widths of the leaves that are far from the source of radiation. Since the radiation beams diverge from the radiation source, the projection widths of at least a portion of the first set of leaves and the projection widths of at least a portion of the second set of leaves when they are projected onto a plane (e.g., a plane 870 shown in FIG. 8) parallel to the first direction and the second direction (e.g., parallel to the isocentric plane) may be equal due to the radiation source being located at a single focus point. For example, the projection widths of the leaves projected onto the isocentric plane are uniform.

In the MLC, the leaves of the same set may have a same cross section, for example, a rectangle, a trapezoid, a trapezoidal trapezoid, a parallelogram, or the like. In some embodiments, a leaf may have a trapezoidal cross section. In some embodiments, at least a portion of the first set of leaves may have a cross section that is different from another portion of the first set of leaves. In some embodiments, at least a portion of the second set of leaves may have a cross section that is different from another portion of the second set of leaves. In some embodiments, at least some of the first set of leaves may have a cross section that is different from at least some of the second set of leaves.

In some embodiments, the MLC may include a single first box in the first plane where the first set of leaves are mounted and a single second box in the second plane where the second set of leaves are mounted. The first/second box may include two compartments each having a sub-set of the first/second set of leaves, respectively. In some embodiments, the MLC may include a pair of first boxes in the first plane and a pair of second boxes in the second plane. In each of the pair of first boxes, a first set of leaves may be mounted in a first cavity 610-1 in the first box. Similarly, in each of the pair of second boxes, a second set of leaves may be mounted in a second cavity 640-1 in the second box.

Figure 7:
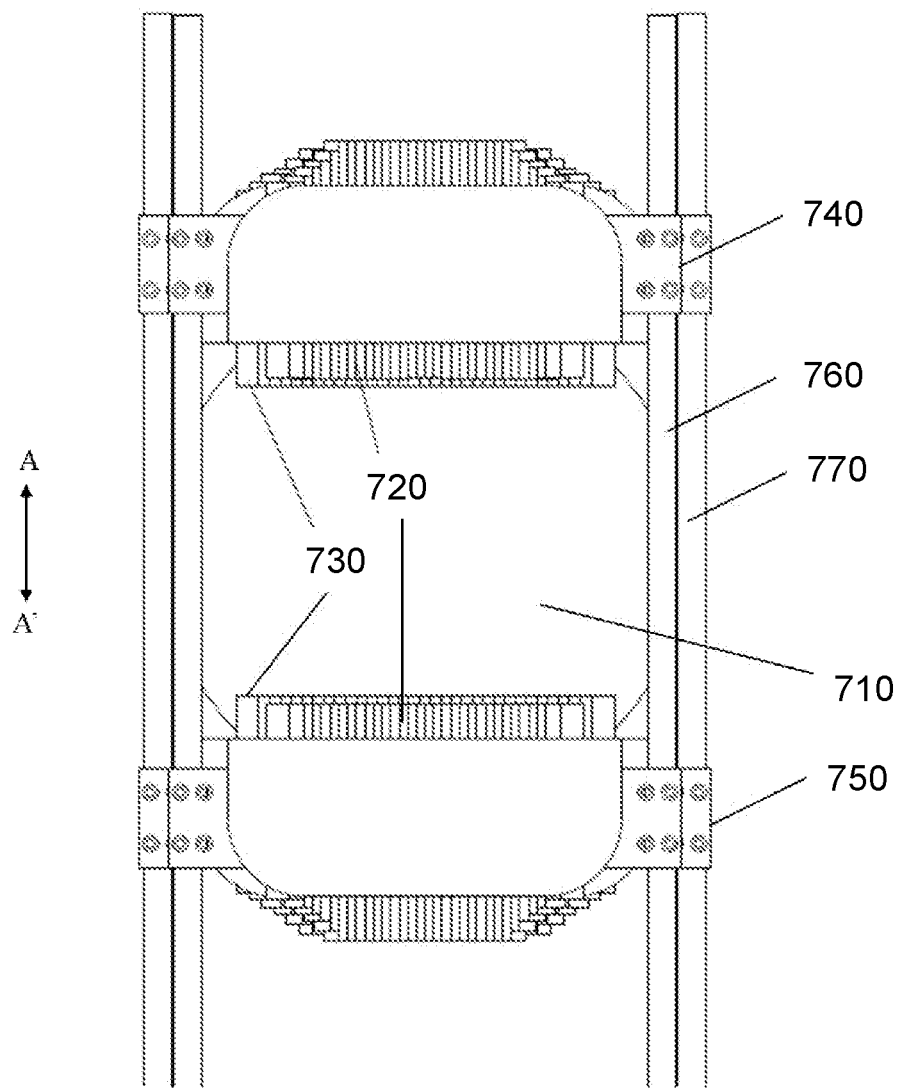
FIG. 7 is a top view of an exemplary MLC according to some embodiments of the present disclosure.

FIG. 7 is a top view of an exemplary MLC according to some embodiments of the present disclosure. The two sets of leaves may be used in an RT device. As shown in FIG. 7, the radiation field 710 may be a region of radiation beams to be limited. A plane of this region is parallel to the isocentric plane of the RT device. In the first plane where the first set of leaves are located, the MLC may include two boxes (i.e., the first sets of boxes) and two sets of leaves (i.e., the first sets of leaves) disposed on both sides of the radiation field 710; and in the second plane where the second set of leaves are located, two boxes (i.e., the second sets of boxes) and two sets of leaves (i.e., the second sets of leaves) are disposed on both sides of the radiation field 710. The two boxes in each of the first plane and the second plane may be symmetrically disposed with respect to the second direction. Alternatively or additionally, the two sets of leaves in each of the first plane and the second plane may be symmetrically disposed with respect to the second direction. In the MLC, the boxes and the leaves which are symmetrically arranged in the same plane may be referred to as boxes of the same level and the leaves of the same level. For example, the first boxes symmetrically set in an upper plane may be referred to as first level boxes, and the first sets of leaves symmetrically set in the upper plane may be referred to as first level leaves. The second boxes symmetrically set in a lower plane may be referred to as second level boxes, and the second sets of leaves symmetrically set in the lower plane may be referred to as second level leaves. The leaves of the first level leaves 720 and the second level leaves 730 are movable in the first direction. As an example, the AA' direction shown in FIG. 7 may be used to indicate the first direction. The direction of motion of the leaves may be towards the radiation field 710, and may also be away from the radiation field 710.

When a leaf moves toward the radiation field 710, after moving a distance, it may substantially contact a leaf on the other side. Alternatively, an acceptable gap may be maintained between the two leaves. Each leaf may be connected to a corresponding driving device, for example, a drive motor. The driving device may receive motion control signals from a motion controller (e.g., a computer) and drive a leaf to move based on the signals. The corresponding driving device of each leaf may receive separate control signals. Therefore, the motion of the leaves may be independent of each other and unaffected by other leaves.

The boxes in the MLC may be connected to the RT device through a connecting component disposed on both sides. As shown in FIG. 7, the first level boxes may be connected to a first-level rail 760 through a first-level connecting component 740, and the second level boxes may be connected to a second-level rail 770 through a second-level connecting component 750. The first-level connecting component 740 may include connecting elements disposed on both sides of the first-level box, and the second-level connecting component 750 may include connecting elements disposed on both sides of the second-level box. The rails 760 and 770 may be parallel to the first direction. Thus, the boxes in the MLC may move, with respect to each other in the first direction, toward the radiation field 710 or away from the radiation field 710. The speed, direction, and distance of the movement of the boxes may be the same or different. The boxes that reach preset positions after movement may be symmetrically or unsymmetrically disposed on both sides of the radiation field 710. It may be appreciated that the faster the leaves of the MLC reach their respective predetermined positions, the shorter the time is needed to form the final therapeutic radiation field when the range of the radiation beams are limited. In the present disclosure, the mobility of the box may reduce the amount of movement of the leaves (i.e., by reducing the moving distance of the leaves with respect to the box where the leaves are mounted), allowing a desired therapeutic radiation field to be formed more quickly, which in turn may reduce treatment time. In some embodiments, radiation towards an undesired region of the subject may also be reduced.

In conjunction with the description of FIG. 4, the center of the radiation field 710 is on the main optical axis of the radiation beams, and the centerline of the radiation field 710 may be parallel to the centerline of the radiation field 410 formed by projected the radiation beams onto the isocentric plane. The primary optical axis may coincide with the line connecting the radiation source and the isocenter, and the isocentric plane may be a plane that passes through the isocenter and is perpendicular to the main optical axis. After the MLC is installed, the centerline of each box may align with the centerline of the radiation field 710. The centerline of the box may refer to the intersection of the symmetric plane of the two sides of the box with the symmetric plane of the upper and lower sides of the box. For example, the centerline of the box may align with the horizontal axis of the radiation field 710. The "alignment" may mean that the two axes coincide with each other, or are parallel to each other and one directly above the other (e.g., along the direction of the main optical axis of the radiation beams).

At least one of the first box and the second box of the MLC may rotate after installation. For example, the rails 760 and 770 are separately rotatable. The rotation of the slide rail may drive the first box and the second box connected thereto to rotate, respectively. The axis of rotation of the first box and the second box may be the main optical axis of the radiation beams. The angle of rotation may be arbitrary. Referring back to FIG. 7, as shown in FIG. 7, the two sets of MLCs are mounted in an upper plane and a lower plane. The upper plane and the lower plane may be parallel to the isocentric plane. The boxes of the MLC may rotate to either side of the radiation field 710, for example, to the left and right sides of the radiation field 710, respectively. The first level boxes and the second level boxes may rotate independently, and the angle of rotation may be different or the same. The movement of boxes of different planes may have no effect on each other. Since the leaves are mounted in the box, the rotation of the box may simultaneously drive the leaves inside thereof to rotate around the main optical axis of the radiation beams.

In some embodiments, the movement of one or more leaves in the MLC and/or one or more boxes in the MLC may be controlled according to controlling signals received, for example, from the processing device 140 (or the processor 210). In some embodiments, each of the one or more leaves may be controlled to move independently for modulating the therapeutic radiation field. In some embodiments, each of the one or more boxes in the MLC may be controlled to move independently. For instance, the controlling signals for the driving device(s) for each leaf in the MLC may indicate a desired position, a moving direction, a moving distance, or the like, or any combination thereof. As another example, the controlling signals for the driving device(s) for each of the one or more boxes in the MLC may indicate a desired position, a moving direction, a moving distance, a rotation angle, or the like, or any combination thereof. By controlling the positions of the leaves in the MLC and/or the box(es) in the MLC, the shape of the aperture that allows radiation beams to pass through may be adjusted. In some embodiments, the processing device 140 (or the processor 210) may be integrated into an RT device (e.g., the RT device 110). In some embodiments, the processing device 140 may generate a set of controlling signals for multiple parts of the RT device, such as a couch, a gantry, the radiation source, the MLC, etc.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
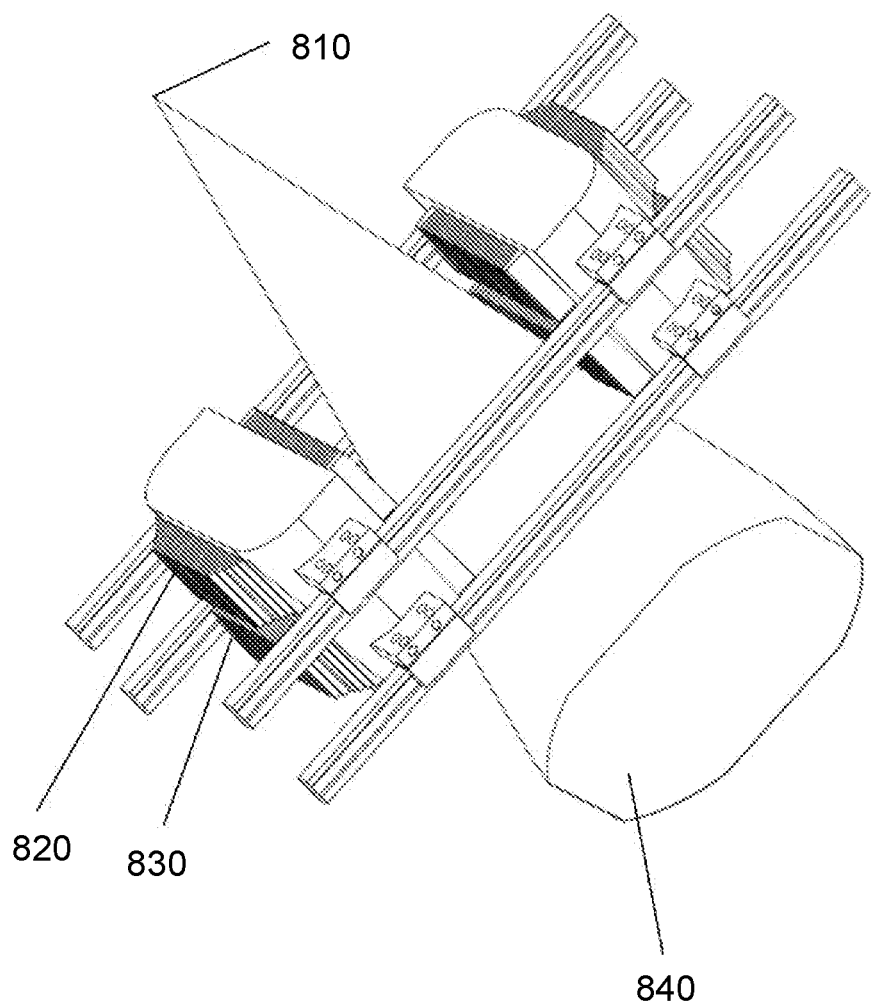
FIG. 9 is an oblique view of an exemplary MLC according to some embodiments of the present disclosure.

FIG. 8 is a side view of an exemplary MLC according to some embodiments of the present disclosure. FIG. 9 is an oblique view of an exemplary MLC according to some embodiments of the present disclosure. A radiation source 810 is shown in FIG. 8 and FIG. 9. The range of the cone beams formed by the radiation beams after passing through the primary collimator may be further limited by the leaves of the MLC (e.g., the first level leaves and the second level leaves). The numeral 820 indicates the first set of leaves, and 830 indicates the second set of leaves. The first set of leaves 820 are mounted directly above the second set of leaves 830. It may be understood that the size of the radiation field formed by the cone beams is related to the distance between the source of the radiation and the center of the radiation field. The larger the distance, the larger the radiation field. Since the two-level leaves are mounted on different planes (e.g., the second set of leaves 830 are directly below the first set of leaves 820), the width of the leaves contained in the second set of leaves 830 may be larger than the width of the leaves included in the first set of leaves 820, so as to conform to the larger radiation field in the second plane (as compared to the radiation field in the first plane). The radiation field 840 is the maximum therapeutic radiation field that the radiation beams can form on the isocentric plane without being limited by the MLC. When the MLC limits the radiation beams, the width projected by the first set of leaves 820 onto the isocentric plane and the width projected by the second set of leaves 830 onto the isocentric plane are the same. In conjunction with the description of the current disclosure where the leaves are staggered in the upper and lower planes, the leaves of the MLC may provide higher resolution at the boundaries of the radiation field.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A multi-leaf collimator, comprising:
a set of leaves installed in a cavity, each leaf of the set of leaves having a length along a first direction and being movable along the first direction, at least a portion of the set of leaves extending beyond the cavity along the first direction, wherein
the set of leaves are arranged along a second direction, the second direction being perpendicular to the first direction; and
a length of a target leaf of the set of leaves is less than a length of a reference leaf of the set of leaves, wherein the target leaf is located in an end portion of the set of leaves along the second direction.

2. The multi-leaf collimator of claim 1, wherein the set of leaves include a plurality of target leaves located at both end portions of the set of leaves along the second direction.

3. The multi-leaf collimator of claim 1, wherein the set of leaves include
a group of reference leaves of a same length, and
a plurality of target leaves located on both sides along the second direction of the group of reference leaves, wherein lengths of at least two of the plurality of target leaves are different from each other.

4. The multi-leaf collimator of claim 3, wherein the lengths of the at least two of the plurality of target leaves gradually increase or decrease along the second direction.

5. The multi-leaf collimator of claim 1, further comprising a box, wherein the cavity is within the box, and a dimension of at least one end portion of the box is less than a dimension of a middle portion of the box.

6. The multi-leaf collimator of claim 1, wherein:
each leaf of the set of leaves is located in a leaf plane, and
a plurality of leaf planes intersect substantially at a focus point.

7. The multi-leaf collimator of claim 1, further comprising:
a second set of leaves installed in a second cavity, each leaf of the second set of leaves having a length along the first direction and being movable along the first direction, at least a portion of the second set of leaves extending beyond the second cavity along the first direction, wherein
the second set of leaves are arranged along the second direction,
a length of a second target leaf of the second set of leaves is less than a length of a second reference leaf of the second set of leaves, wherein the second target leaf is located in an end portion of the second set of leaves along the second direction,
the set of leaves are disposed in a first plane, and
the second set of leaves are disposed in a second plane, the second plane being different from the first plane.

8. The multi-leaf collimator of claim 7, wherein the second set of leaves include a plurality of second target leaves located in both end portions of the second set of leaves along the second direction.

9. The multi-leaf collimator of claim 8, wherein the lengths of the at least two of the plurality of second target leaves gradually increase or decrease along the second direction.

10. The multi-leaf collimator of claim 7, wherein the second set of leaves include
a group of second reference leaves of a same length, and
a plurality of second target leaves located on both sides along the second direction of the group of second reference leaves, wherein lengths of at least two of the plurality of second target leaves are different from each other.

11. The multi-leaf collimator of claim 7, further comprising a second box, wherein the second cavity is within the second box, and a dimension of at least one end portion of the second box is less than a dimension of a middle portion of the second box.

12. The multi-leaf collimator of claim 7, wherein the set of leaves and the second set of leaves are staggered such that radiation that leaks through an inter-leaf space between a pair of neighboring leaves of at least some of the set of leaves is at least partially blocked by a leaf of the second set of leaves.

13. The multi-leaf collimator of claim 7, wherein:
each leaf of the second set of leaves is located in a second leaf plane, and
a plurality of second leaf planes intersect substantially at a second focus point.

14. The multi-leaf collimator of claim 7, wherein a width of each of at least some of the set of leaves projected onto a third plane is the same as a width of each of at least some of the second set of leaves projected onto the third plane, wherein the third plan is parallel to the first direction and the second direction.

15. A radiation therapy (RT) device including a multi-leaf collimator, wherein the multi-leaf collimator includes:
a set of leaves installed in a cavity, each leaf of the set of leaves having a length along a first direction and being movable along the first direction, at least a portion of the set of leaves extending beyond the cavity along a first direction, wherein
the set of leaves are arranged along a second direction, the second direction being perpendicular to the first direction, and
a length of a target leaf of the set of leaves is less than a length of a reference leaf of the set of leaves, wherein the target leaf is located in an end portion of the set of leaves along the second direction.

16. The RT device of claim 15, wherein the multi-leaf collimator includes:
a second set of leaves installed in a second cavity, each leaf of the second set of leaves having a length along the first direction and being movable along the first direction, at least a portion of the second set of leaves extending beyond the second cavity along the first direction, wherein
the second set of leaves are arranged along the second direction,
a length of a second target leaf of the second set of leaves is less than a length of a second reference leaf of the second set of leaves, wherein the second target leaf is located in an end portion of the second set of leaves along the second direction, the set of leaves are disposed in a first plane, and the second set of leaves are disposed in a second plane, the second plane being different from the first plane.

17. The RT device of claim 16, wherein the multi-leaf collimator includes:
   a first pair of boxes that are symmetrically disposed with respect to the second direction, wherein each of the first pair of boxes includes the cavity where the set of leaves are located; and
   a second pair of boxes that are symmetrically disposed with respect to the second direction, wherein each of the second pair of boxes includes the second cavity where the second set of leaves are located, and
   each box of the first pair of boxes and the second pair of boxes is movable along the first direction.

18. The RT device of claim 16, wherein a width of each of at least some of the set of leaves projected onto a third plane is the same as a width of each of at least some of the second set of leaves projected onto the third plane, the third plane being an isocentric plane.

19. The RT device of claim 15, wherein the set of leaves include:
   a group of reference leaves of a same length, and
   a plurality of target leaves located on both sides along the second direction of the group of reference leaves, wherein lengths of at least two of the plurality of target leaves are different from each other.

20. The RT device of claim 19, wherein the lengths of the at least two of the plurality of target leaves gradually increase or decrease along the second direction.

* * * * *